(12) United States Patent
Sabesan

(10) Patent No.: US 7,629,000 B2
(45) Date of Patent: Dec. 8, 2009

(54) METHOD FOR MAKING ANTIMICROBIAL POLYESTER-CONTAINING ARTICLES WITH IMPROVED WASH DURABILITY AND ARTICLES MADE THEREBY

(75) Inventor: Subramaniam Sabesan, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 834 days.

(21) Appl. No.: 10/842,186

(22) Filed: May 10, 2004

(65) Prior Publication Data

US 2004/0247652 A1 Dec. 9, 2004

Related U.S. Application Data

(60) Provisional application No. 60/470,007, filed on May 13, 2003.

(51) Int. Cl.
*A01N 25/34* (2006.01)
(52) U.S. Cl. ........................................ 424/404
(58) Field of Classification Search .................. 424/404
See application file for complete search history.

(56) References Cited

U.S. PATENT DOCUMENTS

| 6,524,508 B1 * | 2/2003 | Ohnishi et al. ............... 264/182 |
| 2003/0017194 A1 | 1/2003 | Joerger et al. |
| 2003/0091612 A1 | 5/2003 | Sabesan |
| 2003/0152632 A1 | 8/2003 | Sabesan et al. |
| 2005/0012630 A1 | 1/2005 | Misato |

FOREIGN PATENT DOCUMENTS

| EP | 0 608 095 | 7/1994 |
| WO | WO 00/49219 | 8/2000 |
| WO | WO 01/88019 | 11/2001 |
| WO | WO 2005/019315 A1 | 3/2005 |

OTHER PUBLICATIONS

International Search Report and the Written Opinion of the International Searching Authority Dated Nov. 11, 2004, International Appln. No. PCT/US2004/014950, International Filing Date: May 12, 2004, Dupont.

* cited by examiner

*Primary Examiner*—Gollamudi S. Kishore
*Assistant Examiner*—Snigdha Maewall
(74) *Attorney, Agent, or Firm*—Gail D. Tanzer

(57) ABSTRACT

The invention relates to antimicrobial polyester-containing articles utilizing chitosan and chitosan-metal complexes, whose wash durability is improved by covalently bonding the chitosan species to the polyester. The invention also relates to the methods of preparing said articles.

30 Claims, 4 Drawing Sheets

METHOD FOR MAKING ANTIMICROBIAL POLYESTER-CONTAINING ARTICLES WITH IMPROVED WASH DURABILITY AND ARTICLES MADE THEREBY

FIELD OF THE INVENTION

This invention relates to antimicrobial polyester-containing articles utilizing chitosan and chitosan-metal complexes, whose wash durability is improved by covalently bonding the chitosan species to the polyester. The invention also relates to the methods of preparing said articles.

TECHNICAL BACKGROUND OF THE INVENTION

This invention relates to the use of chitosan and chitosan-metal complexes to generate antimicrobial polyester-containing articles having improved wash durability.

PCT application WO 00/49219 discloses the preparation of substrates with biocidal properties. The deposition of solubilized chitosan on polyester, among other materials, followed by treatment with silver salts, reduction of the silver salt and crosslinking the chitosan is disclosed to yield a durable biocidal article. The application also discloses the crosslinking of the chitosan after it is applied, either before or after the silver salt treatment.

S. Matsukawa et al., *Sen-I Gakkaishi*, 51(1), 51-56 (1995) disclose the modification of polyester fabrics using chitosan. The polyester was hydrolyzed with caustic soda, neutralized with 1-% acetic acid solution, then treated with a chitosan solution and, optionally, with a crosslinking agent. This method suffers the limitations that no covalent bond is established between the chitosan and the polyester, it is a multistep process, and multiple padding of chitosan is needed to obtain the desired durability.

Huh et al., *J. Appl. Polymer Sci.*, 81, 2769-2778 (2001) disclose grafting of acrylic acid units to a polyester article, followed by activation of the surface carboxyl groups and covalently linking chitosan. This addition of the acrylic oligomeric unit may not be desirable in many textile applications and may not be suitable as a drop-in process for textile mills.

PCT Application WO 01/88019 discloses the use of carbodiimide species to activate polyester carbonyl groups for subsequent covalent bonding with chitosan. The end carboxyl group of a polylactide or caprolactone polymer is treated with N-hydroxysuccinimide and carbodiimide to make an active ester. This active ester is then treated with chitosan to make an amide linkage. The patent does not disclose antimicrobial properties, nor the durability of such properties.

SUMMARY OF THE INVENTION

This invention provides an antimicrobial polyester-containing article having chitosan covalently bonded onto the article by hydrolyzing the polyester followed by a single step amidation of the hydrolyzed polyester using a water-soluble carbodiimide with no intermediate N-hydroxysuccinimide ester. The treatment can be carried out at room temperature. The lack of a need for high-temperature curing simplifies the process and also better preserves the color of the fabric. The article retains its antimicrobial properties after repeated laundering.

Further disclosed is a process for preparing antimicrobial polyester-containing articles comprising the sequential steps of:

(a) providing a polyester-containing article;
(b) contacting the polyester-containing article with a basic solution;
(c) optionally, washing the article produced in step (b);
(d) contacting the article produced in step (b) or step (c) with a strong mineral acid solution;
(e) optionally, washing the article produced in step (d) with water;
(f) contacting the article produced in step (d) or step (e) with a solution comprising a water-soluble, N,N'-disubstituted carbodiimide
(g) optionally, washing the article produced in step (f) with water
(h) contacting the article produced in step (f) or step (g) with a solution comprising a chitosan agent selected from the group consisting of chitosan, chitosan salts and chitosan derivatives;
(i) optionally, heating the article produced in step (I).

Further disclosed is a continuous process for producing an antimicrobial polyester-containing article comprising the sequential steps of:

(a) providing a feed station on which is disposed a polyester-containing article and a take-up station capable of receiving the polyester-containing article;
(b) drawing the article from the feed station through a first treatment station wherein said article is exposed to a basic solution;
(c) optionally, drawing the step (b)-treated article through a second treatment station wherein the article is exposed to water;
(d) drawing the step (b)- or step (c)-treated article through a third treatment station wherein the article is exposed to a strong mineral acid solution;
(e) optionally, drawing the step (d)-treated article through a fourth treatment station wherein the article is exposed to deionized water;
(f) drawing the step (d)- or step (e)-treated article through a fifth treatment station wherein the article is exposed to a solution comprising a water-soluble, N,N'-disubstituted carbodiimide;
(g) optionally, drawing the step (f)-treated article through a sixth treatment station wherein the step (f)-treated article is exposed to water;
(h) drawing the step (f)- or (g)-treated article through a seventh treatment station wherein is exposed to a solution comprising a chitosan agent selected from the group consisting of chitosan, chitosan salts and chitosan derivatives;
(i) optionally, heating the step (h)-treated article after it exits the seventh treatment station; and
(j) causing the step (h)- or step (i)-treated article to be received on and accumulate on the take-up station.

BRIEF DESCRIPTION OF THE DRAWINGS

The drawings consist of four figures as follows.

DETAILED DESCRIPTION OF THE INVENTION

Figure 1:
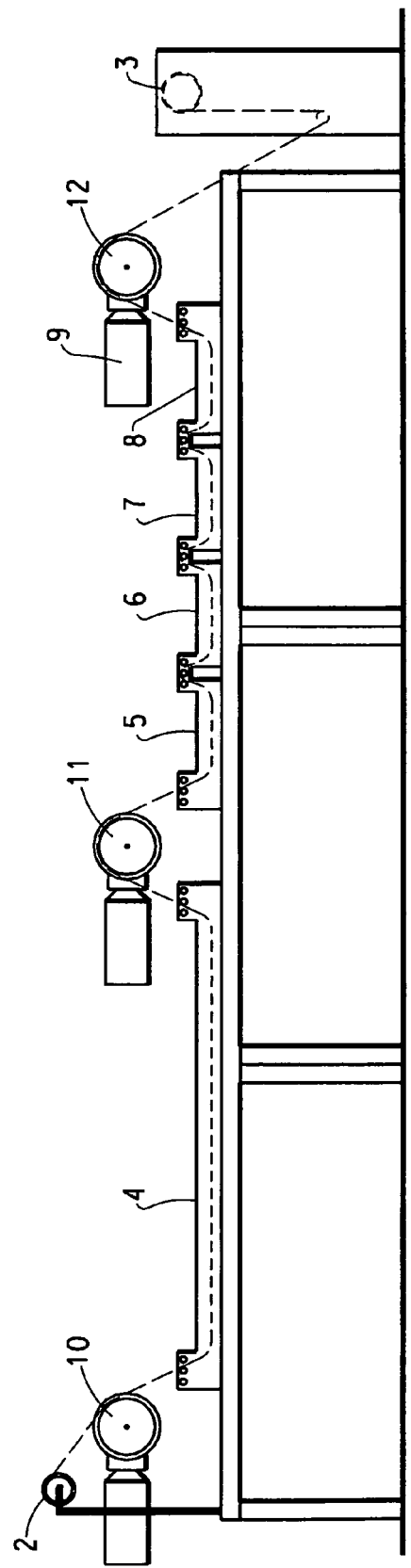
FIG. 1 is a schematic diagram of the continuous process of the invention for making antimicrobial polyester-containing articles.

The present invention involves the preparation of antimicrobial polyester-containing articles that have chitosan covalently bonded thereon. Chitosan is the commonly used name for poly-[1-4]-β-D-glucosamine. Chitosan is chemically derived from chitin, which is a poly-[1,4]-β-N-acetyl-D-glucosamine which, in turn, is derived from the cell walls of fungi, the shells of insects and, especially, crustaceans. As used herein, the term "covalently bonded" means that the chitosan is bound to the polyester substrate by covalent bonding, in which electrons contributed from each atom participating in the bond are shared, as opposed to ionic (electrostatic) bonding. The functionality needed for covalent attachment of chitosan to the polyester is accomplished by hydrolysis with base followed by mineral acid treatment of the article. Subsequently, the carboxyl group is activated with a water-soluble, N,N'-disubstituted carbodiimide, and the chitosan is attached directly to the terephthalic acid containing polymer chain.

Polyesters comprise those polymers prepared from diols and dicarboxylic acids. Dicarboxylic acids useable in the preparation of polyesters include, but are not limited to, unsubstituted and substituted aromatic, aliphatic, unsaturated, and alicyclic dicarboxylic acids and the lower alkyl esters of dicarboxylic acids having from 2 carbons to 36 carbons. Specific examples of the desirable dicarboxylic acid component include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,11-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, metal salts of 5-sulfo-dimethylisophalate, fumaric acid, maleic anhydride, maleic acid, hexahydrophthalic acid, phthalic acid and the like and mixtures derived therefrom.

Diols useful in the preparation of polyesters include, but are not limited to, unsubstituted, substituted, straight chain, branched, cyclic aliphatic, aliphatic-aromatic or aromatic diols having from 2 carbon atoms to 36 carbon atoms. Specific examples of the desirable diol component include ethylene glycol, 1,3-propanediol, 1,2-propanediol, 1,2-, 1,3- and 1,4-butanediol, 1,5-pentane diol, 1,6-hexanediol, 1,8-octanediol, 1,10-decanediol, 1,12-dodecanediol, 1,14-tetradecanediol, 1,16-hexadecanediol, dimer diol, isosorbide, 4,8-bis(hydroxymethyl)-tricyclo[5.2.1.0/2.6]decane, 1,2-, 1,3- and 1,4-cyclohexanedimethanol, and the longer chain diols and polyols made by the reaction product of diols or polyols with alkylene oxides including di(ethylene glycol), tri(ethylene glycol), poly(ethylene ether) glycols, poly(butylene ether) glycols and the like and mixtures derived therefrom.

The preferred polyesters useful herein are poly(ethylene terephthalate) ("2GT"), poly(trimethylene terephthalate) ("3GT"), and blends and copolymers thereof.

The term "polyester-containing article" as used herein means an article that has a surface composition of at least 10% polyester by area.

In apparel applications, garments comprising polyester often include other components, such as acrylic, wool, silk, cotton, linen, flax, hemp, rayon, cellulose, wood pulp, cellulose acetate or triacetate, nylon 6 or nylon 66, poly(m-phenylene isophthalamide) ('PMIA,' available from E. I. du Pont de Nemours and Company, Wilmington, Del., USA under the trademark Nomex®), poly(p-phenylene terephthalamide) ('PPTA,' available from E. I. du Pont de Nemours and Company under the trademark Kevlar®), polyolefins such as polypropylene and polyethylene, fiberglass, Lycra® spandex (available from E. I. du Pont de Nemours and Company), and elastomers. Polyesters other than poly(ethylene terephthalate) may also be present, for example, a copolymer with a low melt temperature that is used as a binder fiber in fiberfill.

Combination of the fibers listed above can be used in the present invention for added benefits. Such fiber combinations can be prepared by any means known to those skilled in the art. "Bicomponent" filaments in which two polymers are arranged side-by-side or in a sheath-core arrangement can be formed during the spinning process. 2GT/3GT bicomponent fibers such as are disclosed in U.S. Pat. No. 3,671,379, herein incorporated by reference, are one example useful in the present invention.

Another means of preparing fiber combinations is by intimate blending of staple fibers; i.e., as the staple yarn is spun, the different fibers can be combined in either a carding or drawing process. Fiber combinations can also be prepared by knitting or weaving yarns, staple, or filament of different composition into the same fabric. In the case of Lycra® spandex (E. I. de Nemours and Company, Wilmington, Del.), the spandex is added in staple yarn at either the spinning step or during fabric production, such as plating in knitting.

As a first step of the process of the present invention, polyester-containing articles are pretreated. This pretreatment involves hydrolyzing the surface of said polyester-containing article to prepare it for subsequent attachment of chitosan groups. The pretreatment is achieved by the hydrolytic rupture of some of the ester bonds in the polyester-containing articles to generate carboxylate groups.

The hydrolysis treatment involves exposure of the polyester-containing article to an aqueous solution of a base. All soluble Group I, II, and III hydroxides, ammonium hydroxide, and alkyl-substituted ammonium hydroxides can be used to effect hydrolysis. The base can be dissolved in water or a mixture of water with one or more water-soluble organic solvents. Examples of suitable water-soluble organic solvents include methanol, ethanol, propanol, ethylene glycol, propylene glycol, acetonitrile, dimethylformamide, and dimethylacetamide.

The base useful in the invention is typically an alkali metal hydroxide, most preferably sodium hydroxide. The concentration of base in the aqueous solution is not critical and depends on the base being used and the treatment temperature. In the case of sodium hydroxide, the concentration may range from 1 to 40% by weight. The temperature of the treatment is not critical, room temperature being preferred. Temperature ranges of 10 to 90° C. may be employed. Lower temperature is preferred with the higher concentrations of base. The article is exposed to the basic solution long enough to reduce its weight by from 1 to 30 percent, preferably by from 1 to 10 percent. The treatment time will depend on the concentration and temperature of the basic solution; the higher the concentration of the base solution, and the higher the temperature employed the shorter the time of treatment. Times as low as 2 to 30 seconds can be employed successfully. Optionally, the article is then washed with water to remove the bulk of the base solution.

Following the hydrolysis treatment, the article is acidified by treatment with strong mineral acid to a pH of less than or equal to the pKa of the carboxylate groups generated by the hydrolysis treatment. The article can be directly acidified with aqueous mineral or organic acids without the involvement of water washing. However, aqueous washing is preferred to minimize the use of acids. As used herein, the term "strong" mineral acid, means acids having a pH less than pH 2. Mineral acids useful herein include, for example, hydrochloric, sulfuric and phosphoric acids. Hydrochloric acid is most preferred. The time and temperature of the acidification step are not critical; times ranging from 2 seconds to 30 minutes at room temperature can be employed successfully. As will be apparent to one skilled in the art, the time and temperature of the hydrolysis treatment and the appropriate concentration of the base solution to use will also be affected by the overall composition of the article, since, as described above, the polyester may be combined with a wide variety of other components in the article being treated.

Optionally, the article is again washed with water to remove the bulk of the mineral acid. The article may then be used directly in the next step, or may, optionally, be dried.

While not desiring to be bound by any particular theory, it is believed that the acidification below the pKa of the carboxylate groups, resulting in the formation of the free carboxylic acid group, greatly increases the rate and efficacy of the reaction of the carboxyl species with chitosan in the subsequent step.

Following the acidification step, the article is treated with an aqueous solution of a water-soluble, N,N'-disubstituted carbodiimide. By "carbodiimide" is meant a derivative of the compound having the general formula $R^1N=C=NR^2$, where $R^1$ and $R^2$ may be identical or different. For example, dicyclohexylcarbodiimide is $C_6H_{11}-N=C=N-C_6H_{11}$ (see Rule C-956 in Nomenclature in Organic Chemistry, International Union of Pure and Applied Chemistry, Butterworth & Co., (London, UK) (1971), p. 295). "R" denotes a univalent radical attached by means of carbon and derived from aliphatic, carbocyclic, or heterocyclic compounds, which may be saturated or unsaturated, and unsubstituted or substituted, but it is not used for —CN, —CNO, —CNS, or —CNSe groups or for groups attached directly through >C=X where X is O, S, Se, Te, NH, or substituted NH (Ibid., p. 80). One preferred such carbodiimide is 1-ethyl-3-(3-dimethylaminopropyl)carbodiimide (EDC), which is available commercially as the hydrochloride salt from, for example, Advanced Chemtech (Louisville, Ky.). Suitable concentrations are 0.01 to 2-weight % by volume, preferably 0.1 w/v %. The reaction can be run from about 20 to 80° C., preferably run at room temperature. Exposure time can range from about 5 seconds to about 60 minutes, preferably about 6 seconds for fiber and about 30 minutes for fabrics. Following the treatment with carbodiimide, the article is optionally washed with water.

The article is then treated with chitosan. This comprises soaking or wetting the article with a solution containing a chitosan agent. The term "chitosan agent" as used herein means all chitosan-based moieties, including chitosan, chitosan salt, and chitosan derivatives. The solution comprising the chitosan agent may be aqueous. However, since chitosan by itself is not soluble in water, the chitosan may be solubilized in a solution. Solubility is obtained by adding the chitosan to a dilute solution of a water-soluble, organic acid selected from the group consisting of mono-, di- and polycarboxylic acids. This allows the chitosan to react with the acid to form a water-soluble salt, herein referred to as "chitosan salt." Alternatively, "chitosan derivatives," including N- and O-carboxyalkyl chitosan, that are water-soluble, can be used directly in water instead of chitosan salt. The chitosan may also be dissolved in special solvents like dimethylacetamide in the presence of lithium chloride, or N-methyl-morpholine-N-oxide. Such solubilized chitosan solutions can be used in the present invention instead of aqueous solutions containing chitosan salt or chitosan derivatives.

Typically, the chitosan solution is an aqueous acetic acid solution, for example, an aqueous solution containing 2% chitosan and 0.75% acetic acid or 2% chitosan and 1.5% aqueous acetic acid. The time of treatment is typically 5 to 30 minutes. The temperature of the treatment is not critical, room temperature being preferred. After treatment with chitosan solution, excess solution may be allowed to drip out, or may be removed by wringing or spinning.

Optionally, the treated article is then dried via oven drying or a combination of ambient air drying and oven drying.

Optionally, the article is then heated in air or nitrogen at a temperature in the range of room temperature to 190° C., preferably at room temperature for about 24 hours or at about 110° C. for about one hour.

Articles prepared by the above methods exhibit antimicrobial properties and retain such properties after much laundering, as illustrated in the Examples below. The term "antimicrobial" as used herein means both bactericidal and fungicidal. In addition, polyester-containing fibers and yarns processed herein exhibit favorable physical properties with respect to tenacity, elongation and hand-feel.

Said antimicrobial properties may, optionally, be further enhanced by treatment with soluble metal salts, for example, soluble silver salts, soluble copper salts and soluble zinc salts. The preferred metal salts of the invention are aqueous solutions of zinc sulfate, copper sulfate or silver nitrate. The metal salts are typically applied by dipping or padding a dilute (0.1 to 5%) solution of salt in water. The degree of enhancement depends on the particular metal salt used, its concentration, the time and temperature of exposure, and the specific chitosan treatment, that is, the type of chitosan agent, its concentration, the temperature, and the time of exposure.

Articles prepared by the above method of the invention also exhibit improved antistatic properties. Antistatic properties refer to the ability of a textile material to disperse an electrostatic charge and to prevent the buildup of static electricity. (*Dictionary of Fiber & Textile Technology*, Hoechst Celanese Corp., Charlotte, N.C. (1990), p. 8)

A further optional post-treatment comprises applying a carboxyl-containing polymer to the chitosan treated article, or to the metal salt treated chitosan treated article. The term "carboxyl-containing polymer" as used herein means a polymer that contains carboxylic acid groups in side chains attached to the polymer backbone. The carboxyl-containing polymer, most preferably polyacrylic acid, is typically applied from a dilute aqueous solution by dipping or padding.

Any of the above described chitosan-treated articles, metal salt-treated articles or the carboxyl-containing polymer-treated articles, may benefit from a further chitosan solution treatment. Included within the scope of this invention are articles that, having received a first treatment with chitosan by the process of the present invention, are further subjected to one or more treatments with metal salt, carboxyl-containing polymer and/or additional chitosan in any order, with the proviso that the surface of the final article is treated with metal salt or a chitosan solution.

In a preferred embodiment, the process of the invention further involves heating the chitosan-grafted polyester-containing article to a temperature of from room temperature to 190° C. under a nitrogen or ambient atmosphere for from 30 seconds to 24 hours.

The articles of the present invention can also be produced in a continuous process. The process is illustrated by FIG. 1 of the drawings herein. Referring now to FIG. 1, there is shown an apparatus for performing the following sequential steps of the invention:

(a) A feed station (2) on which is disposed a polyester-containing article (1) is provided. The feed station would typically comprise one or more feed rollers (10).

(b) The article is drawn from the feed station through a first treatment station (4) wherein said article is exposed to a basic solution. The treatment stations herein would typically be immersion bath trays or tanks.

(c) The article is optionally drawn from the first treatment station through a second treatment station (5) wherein the step (b)-treated article is exposed to water. Optionally, one or any number of draw rolls (11) may help guide the article between the treatment stations. Draw rolls such as draw roll (11) may be placed along any step of the continuous process as is commonly known in the art.

(d) The article from the second treatment station is drawn through a third treatment station (6) wherein the step (c)-treated article is exposed to a strong mineral acid solution.

(e) Optionally, the article from the third treatment station is drawn through a fourth treatment station (7) wherein the step (d)-treated article is exposed to water.

(f) The article is then drawn through a fifth treatment station (8) wherein the step (d)- or step (e)-treated article is exposed to a solution comprising the water-soluble, N,N'-disubstituted carbodiimide.

(g) Optionally, the article is then drawn through a sixth treatment station (13) wherein the step (f)-treated article is exposed to water.

(h) The article is then drawn through a seventh treatment station comprising the chitosan agent. As discussed above, the chitosan agent is selected from the group consisting of chitosan, chitosan salts and chitosan derivatives.

(i) Optionally after it exits the chitosan treatment station, the step (h)-treated article may be heated by a heater, such as a heater roll assembly (9).

(j) The step (h)- or step (i)-treated article is then received on and accumulates on the take-up station (3). The treated article would typically be wound by means of a traversing guide (12) onto the take-up station (3) which is typically one or more cardboard or resin tubes to form spinning bobbins.

The feed station, treatment stations, heaters, and take-up components may be any convenient means known in the art for continuous treatment of fibers and yarns (see, for example, *Ullmann's Encyclopedia of Industrial Chemistry*, fifth Edition, Wolfgang Gerhartz, Executive Editor, Volume A10, VCH Verlagsgesellschaftg, Weinheim, Federal Republic of Germany (1987), "Fibers, 3. General Production Technology," H. Lucker, W. Kagi, U. Kemp, and W. Stibal, pp. 511-566). The continuous process is particularly appropriate for treating polyester-containing fiber or yarn on a commercial scale.

The preferred articles of the present invention are in the form of fibers; fabrics, including wovens and nonwovens; filaments; films; and articles and constructs prepared therefrom. By a "nonwoven" fabric is meant a fabric in which the layers of the fabric are comprised of fibers that are not woven into a fabric but rather are formed into a sheet, particularly a tissue.

The antimicrobial articles of the invention shall find application in uses such as apparel, including sportswear, active wear, intimate apparel (e.g., undergarments), swimwear, protective sports pads, and medical garments (e.g., gowns, masks, gloves, head coverings); washable healthcare products, including bandages, medical drapes, and diapers; household articles, including fiberfill, bedding, bed linens, window treatments, carpet and flooring components, upholstery components, towels, washcloths, dust cloths, automotive wipes, household cleaning wipes, counter wipes, mops, tablecloths and surfaces; and food processing/service including food and other containers, cleaning cloths, towels, and surfaces. The term "wipe" as used herein denotes a sheetlike article for wiping a surface, particularly but not only for cleansing said surface.

EXAMPLES

Methods

Laundering

Test specimens were laundered according to the 2A Test procedure of the MTCC Test Method 61.

Antimicrobial Properties

Treated articles were tested for antimicrobial properties by the Shake Flask Test for Antimicrobial Testing of Materials, as follows:

1. A single, isolated colony from a bacterial or yeast agar plate culture was inoculated in 15-25 ml of Trypticase Soy Broth (TSB) in a sterile flask. It was incubated at 25-37° C. (using optimal growth temperature for the specific microbe) for 16-24 hours with or without shaking (selecting appropriate aeration of the specific strain). For filamentous fungi, sporulating cultures were prepared on agar plates.

2. The overnight bacterial or yeast culture was diluted into sterile phosphate buffer (see below) at pH 6.0 to 7.0 to obtain approximately $10^5$ colony forming units per ml (cfu/ml). The total volume of phosphate buffer needed was 50 ml×number of test flasks (including controls). For filamentous fungi, spore suspensions at $10^5$ spores/ml were prepared. Spore suspensions were prepared by gently resuspending spores from an agar plate culture that had been flooded with sterile saline or phosphate buffer. To obtain initial inoculum counts, final dilutions (prepared in phosphate buffer) of $10^{-4}$ and $10^{-3}$ were plated onto Trypticase Soy Agar (TSA) plates in duplicate. Plates were incubated at 25-37° C. overnight.

3. 50 ml of inoculated phosphate buffer was transferred into each sterile test flask containing 0.5 g of material to be tested. Also, control flasks of inoculated phosphate buffer and uninoculated phosphate buffer with no test materials were prepared.

4. All flasks were placed on a wrist-action shaker and incubated with vigorous shaking at room temperature. All flasks were sampled periodically and appropriate dilutions were plated onto TSA plates. The TSA plates were incubated at 25-37° C. for 16-48 hours and colonies were then counted.

5. Colony counts were reported as the number of Colony Forming Units per ml (cfu/ml).

6. The activity constant, $\Delta t$ value, was calculated as follows: $\Delta t = C - B$, where $\Delta t$ is the activity constant for contact time t, C is the mean $\log_{10}$ density of microbes in flasks of untreated control materials after X hours of incubation, and B is the mean $\log_{10}$ density of microbes in flasks of treated materials after X hours of incubation. $\Delta t$ was typically calculated at 4, 6, or 24 hours and may be expressed as $\Delta t_X$.

Stock phosphate buffer:

Monobasic Potassium Phosphate 22.4 g

Dibasic Potassium Phosphate 56.0 g

Deionized Water volume increased to 1000 ml

The pH of the phosphate buffer was adjusted to pH 6.0 to 7.0 with either NaOH or HCl. The stock phosphate buffer was filtered, sterilized, and stored at 4° C. until use. The working phosphate buffer was prepared by diluting 1 ml of stock phosphate buffer in 800 ml of sterile deionized water.

Preparation of Chitosan Grafted 2GT Knit Standard Polyester Fabrics

Polyester fabric was soaked in 10% aqueous sodium hydroxide solution and gently shaken for 90 min. It was then washed with water and soaked in 1 M aqueous hydrochloric acid solution for 30 min, washed with deionized water, and dried in air for 24 h. The fabric was then soaked in an aqueous solution of 0.1% (w/v) of 1-ethyl-3-(3-dimethylaminopropyl)carbodiimide ('EDC') for 3 h. The fabric was then washed with deionized water and immersed in 2-weight % aqueous chitosan solution containing 1.5% acetic acid for 30 minutes. The chitosan was food grade Chitoclear®) chitosan, mol. wt. 75,000, from Primex Ingredients ASA, Norway. The degree of N-deacetylation of the chitosan was over 90% as ascertained by proton and carbon 13 NMR spectroscopy. The molecular weight was estimated using standard relative viscosity measurements as reported in the literature. The excess chitosan solution was squeezed out, and the fabric was air dried for 24 hours. If needed, (Procedure A) the fabric was optionally washed with acetonitrile to remove any organic contaminants that might be present. Procedure B employed no organic solvent wash. The treated fabric was then air dried for 1 h, followed either by heating in air at 110° C. for 1 h or by sitting at ambient temperature (about 25° C.) for at least a day.

Example 1

Chitosan was grafted onto polyester fabric (8 inch×8 inch, 2GT knit fabric weighing 5.59 g) as described above. The weight of the chitosan-treated fabric was 5.73 g, an increase of 0.14 g. Samples that had not been washed with acetonitrile (i.e., Procedure B) were heated in air at 110° C. for one hour or allowed to sit in air at ambient temperature (about 25° C.) for at least a day. Samples that had been washed with acetonitrile (i.e., Procedure A) were heated in air at 110° C. for one hour.

Figure 2:
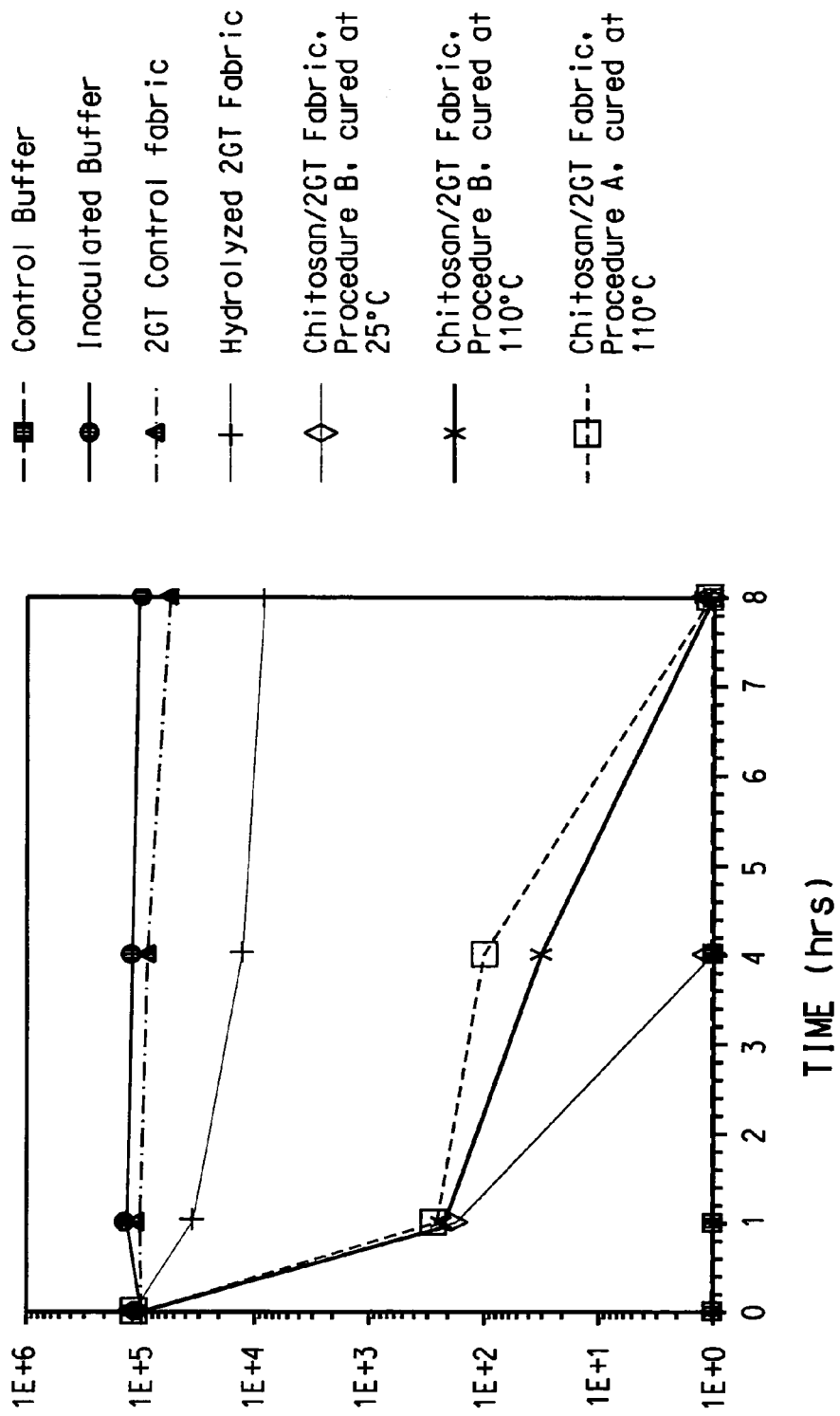
FIG. 2 is a diagram showing the antimicrobial effect vs. *E. coli* ATCC 25922 of polyester fabrics with covalent chitosan conjugation chemistry treatment.

The fabric samples were tested for antimicrobial efficacy as described above, versus *E. coli* ATCC 25922. The data in FIG. 2 clearly show that high temperature curing is not needed to maintain the antimicrobial activity of chitosan on the polyester surface.

Example 2

A small sample of the fabric that had been in prepared in Example 1, using Procedure B and cured at 110° C. for one hour was treated with Orange II dye (0.5 g/l in 0.7% aqueous acetic acid) for 5 min, washed extensively with deionized water, and air dried. The intense orange coloration indicated the presence of chitosan on the fabric. 2GT fabric that was untreated or only treated with caustic did not exhibit such coloration when similarly treated with Orange II dye. After one 2A (equivalent to 5 wash cycles), four 2A (equivalent to 20 wash cycles) and ten 2A (equivalent to 50 wash cycles) washes, the carbodiimide-activated, chitosan-treated fabric was still orange, indicating a considerable amount of chitosan still coated the surface of the polyester fabric.

Example 3

Figure 3:
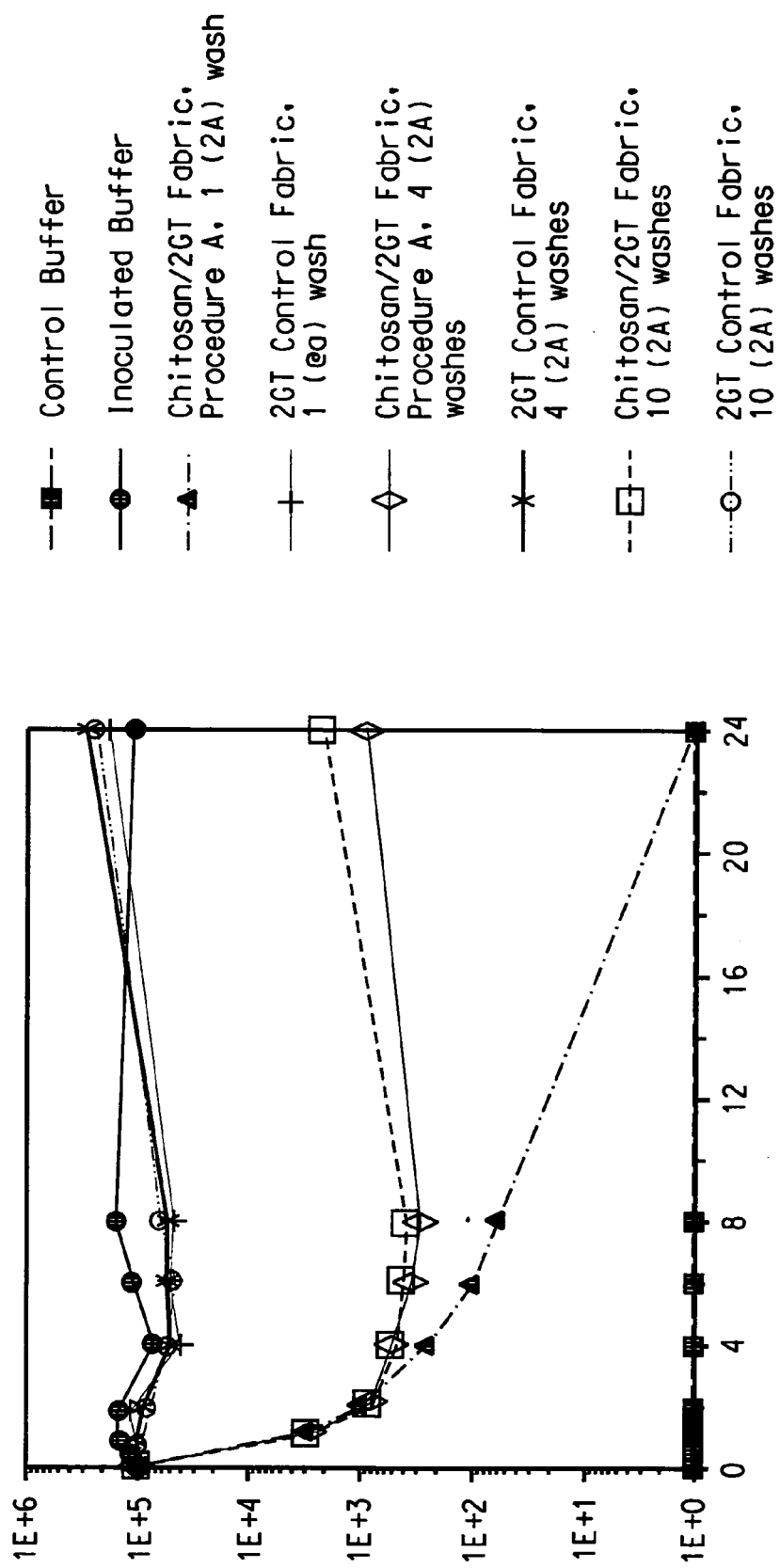
FIG. 3 is a diagram showing the antimicrobial effect vs. *E. coli* ATCC 25922 of polyester fabrics with covalent chitosan conjugation chemistry treatment after laundering (1, 4, and 10 2A wash cycles).

The chitosan-treated 2GT fabric that had been in prepared in Example 1, using Procedure A and cured at 110° C. for one hour, was laundered according to AATCC Test Method 61, Test 2A. Results of antimicrobial testing of washed, carbodiimide-activated, chitosan-treated fabric and a similarly washed 2GT control fabric are shown in FIG. 3. After the equivalent of five wash cycles (i.e., one 2A wash), the chitosan-treated fabric killed all the *E. coli* within 24 hours. Even after the equivalent of fifty wash cycles (ten 2A washes) the chitosan-treated fabric still had antimicrobial activity. The control 2GT fabrics showed no antimicrobial activity.

Example 4

Figure 4:
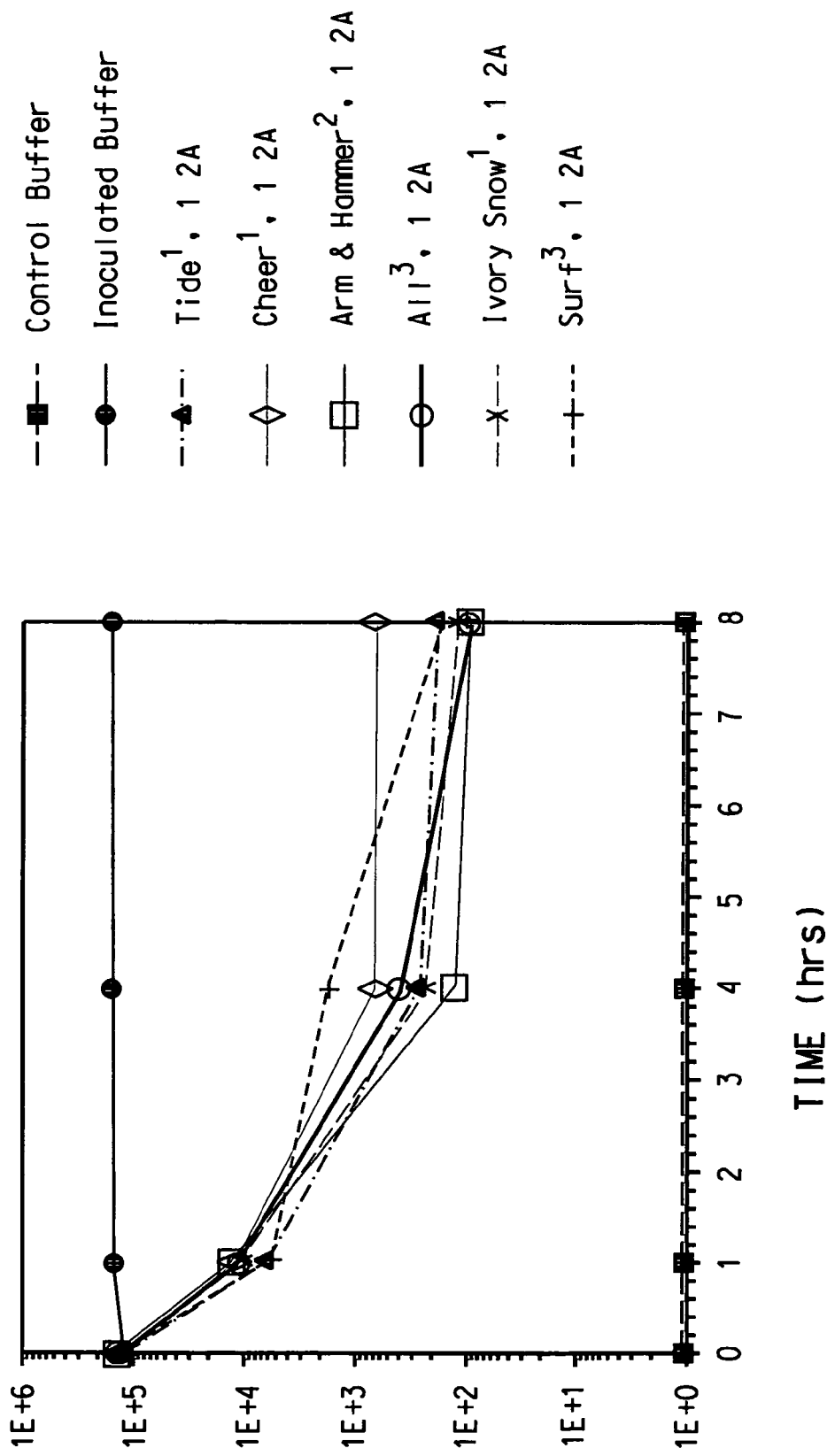
FIG. 4 is a diagram showing the antimicrobial effect vs. *E. coli* ATCC 25922 of polyester fabrics with covalent chitosan conjugation chemistry treatment after laundering with various household detergents.

Carbodiimide-activated, chitosan-treated fabrics prepared as in Example 1, using Procedure B and cured at 110° C. for one hour, were laundered according to AATCC Test Method 61, Test 2A protocol (one 2A wash) with a variety of common household detergents, with similar retention of antimicrobial activity (FIG. 4).

Example 5

Chitosan is grafted onto polyester-containing fabric (60:40 2GT:cotton blend) as in Example 1, using Procedure B with curing at 110° C. for one hour. The treated fabric is made into a dishtowel. A dishtowel is also made from the untreated fabric. A piece of each towel is tested for antimicrobial efficacy as described above. The piece of dishtowel made from treated fabric shows antimicrobial activity against *Staphylococcus aureus* ATCC 6538, *Pseudomonas aeruginosa* ATCC 27853, and *Escherichia coli* ATCC 25922, while the untreated control does not. The treated dish towel is then laundered 10 times according to MTCC Test Method 61, Test 2A and is shown to retain its antimicrobial activity against Staphylococcus aureus ATCC 6538, Pseudomonas aeruginosa ATCC 27853, and Escherichia coli ATCC 25922, Example 6

Twenty six-month-old infants, 10 male and 10 female, for a period of one month, wear a series of cloth diapers containing polyester-containing fibers that have been grafted with chitosan as in Example 1, using Procedure B with curing at 110° C. A similar group of 10 male and 10 female six-month-old infants, for a period of one month, wear a series of cloth diapers that have not been so treated. All diapers are laundered 10 times using Tide® laundry detergent (Proctor & Gamble Company, Cincinnati, Ohio) on a hot wash/cold rinse cycle. Samples from each diaper are tested for antimicrobial efficacy as described above. The samples made from treated fibers show antimicrobial activity against Staphylococcus aureus ATCC 6538, while the untreated ones do not. Also, the incidence of diaper rash among the group wearing treated diapers is lower than the incidence among the control group.

What is claimed is:

1. A method for preparing an antimicrobial polyester-containing article having chitosan covalently bonded thereon, comprising the sequential steps of:
    (a) providing a polyester-containing article;
    (b) contacting the polyester-containing article with a basic solution, thereby causing hydrolytic rupture of ester bonds in the polyester-containing articles to generate carboxylate groups;
    (c) optionally, washing the article produced in step (b);
    (d) contacting the article produced in step (b) or step (c) with a strong mineral acid solution, wherein the pH of acid solution is less than pH 2 and the mineral acid is $HCl$, $H_2SO_4$, or $H_3PO_4$, thereby acidifying the article by formation of free carboxylic acid end groups;
    (e) optionally, washing the article produced in step (d) with water;
    (f) contacting the article produced in step (d) or step (e) with a solution comprising a water-soluble, N,N'-disubstituted carbodiimide;
    (g) optionally, washing the article produced in step (f) with water
    (h) contacting the article produced in step (f) or step (g) with a solution comprising a chitosan agent selected from the group consisting of chitosan, chitosan salts, N-carboxyalkyl chitosan, and O-carboxyalkyl chitosan; and
    (i) optionally, heating-the article produced in step (h).

2. A method for producing an antimicrobial polyester-containing article having chitosan covalently bonded thereon, comprising the sequential steps of:
    (a) providing a feed station on which is disposed a polyester-containing article and a take-up station capable of receiving the polyester-containing article;
    (b) drawing the article from the feed station through a first treatment station wherein said article is contacted with to a basic solution, thereby causing hydrolytic rupture of ester bonds in the polyester-containing articles to generate carboxylate groups;
    (c) optionally, drawing the step (b)-treated article through a second treatment station wherein the article is contacted with water;
    (d) drawing the step (b)- or step (c)-treated article through a third treatment station wherein the article is contacted with a strong mineral acid solution, wherein the pH of acid solution is less than pH 2 and the mineral acid is $HCl$, $H_2SO_4$, or $H_3PO_4$, thereby acidifying the article by formation of free carboxylic acid end groups;
    (e) optionally, drawing the step (d)-treated article through a fourth treatment station wherein the article is contacted with deionized water;
    (f) drawing the step (d)- or step (e)-treated article through a fifth treatment station wherein the article is contacted with a solution comprising a water-soluble, N,N'-disubstituted carbodiimide;
    (g) optionally, drawing the step (f)-treated article through a sixth treatment station wherein the step (f)-treated article is contacted with water;
    (h) drawing the step (f)- or step (g)-treated article through a seventh treatment station wherein the article is contacted with a solution comprising a chitosan agent selected from the group consisting of chitosan, chitosan salts, N-carboxyalkyl chitosan, and O-carboxyalkyl chitosan;
    (i) optionally, heating the step (h)-treated article after it exits the-seventh treatment station; and
    (j) causing the step (h)- or step (i)-treated article to be received on and accumulate on the take-up station.

3. The method of claim 1 or 2 wherein the water-soluble, N,N'-disubstituted carbodiimide is 1-ethyl-3-(3-dimethylaminopropyl)carbodiimide.

4. The method of claim 1 or 2 wherein the concentration of the water-soluble, N,N'-disubstituted carbodiimide is 0.01 to 2 weight % by volume.

5. The method of claim 3 wherein the concentration of the water-soluble, N,N'-disubstituted carbodiimide is 0.1 w/v %.

6. The method of claim 1 or 2 wherein in step (f) the polyester-containing article is contacted with the solution comprising a water-soluble, N,N'-substituted carbodiimide for about 5 seconds to about 60 minutes.

7. The method of claim 1 further comprising contacting the article produced in step (f), (g), (h) or (i) with a solution comprising a metal salt; a solution comprising a carboxyl-containing polymer; an additional solution comprising a chitosan agent; or combinations thereof, wherein the surface of the article produced comprises chitosan, a metal salt, or combinations thereof.

8. The method of claim 2 further comprising drawing the step (f)-, (g)-, (h), or (i)-treated article through a subsequent station containing a solution comprising a metal salt; a solution comprising a carboxyl-containing polymer; an additional solution comprising a chitosan agent; or combinations thereof, wherein the surface of the article produced comprises chitosan, a metal salt or combinations thereof.

9. The method of claim 7 or claim 8 wherein the metal salt is selected from the group consisting of soluble silver salts, soluble copper salts, and soluble zinc salts.

10. The method of claim 7 or claim 8 wherein the carboxyl-containing polymer is polyacrylic acid or sodium carboxymethylcellulose.

11. The method of claim 1 or claim 2 wherein the polyester-containing article is in the form of a filament, fiber, yarn, woven fabric, nonwoven fabric, or film.

12. The method of claim 1 or claim 2 wherein the polyester is selected from the group consisting of poly(ethylene terephthalate), poly(trimethylene terephthalate), poly(tetramethylene terephthalate, and copolymers and blends thereof.

13. The method of claim 1 or claim 2 wherein the polyester-containing article is in the form of a bicomponent fiber consisting essentially of poly(ethylene terephthalate) and poly (trimethylene terephthalate).

14. An antimicrobial polyester-containing article produced by the method of claim 1.

15. An antimicrobial polyester-containing article produced by the method of claim 2.

16. The polyester-containing article of claim 14 or 15 wherein the article is in the form of a filament, fiber, yarn, fabric or film.

17. An item of apparel comprising the antimicrobial polyester-containing article of claim 16.

18. The item of apparel of claim 17 in the form of a swimsuit, sportswear, active wear, protective sports pad, undergarment, or medical garment.

19. The item of apparel of claim 18 wherein the medical garment is a gown, mask, glove, or head covering.

20. A washable health care product comprising the antimicrobial polyester-containing article of claim 16.

21. The washable health care product of claim 20 selected from the group consisting of medical drapes, diapers, and bandages.

22. A container comprising the antimicrobial polyester-containing article of claim 14 or 15.

23. A surface for food processing or food serving comprising the antimicrobial polyester-containing article of claim 14 or 15.

24. A household article comprising the antimicrobial polyester-containing article of claim 14 or 15.

25. The household article of claim 24 selected from the group consisting of fiberfill, bedding, bed linens, window treatments, carpet and flooring components, upholstery components, sheets, automotive wipes, household cleaning wipes, counter wipes, towels, washcloths, dust cloths, mops, tablecloths, and surfaces.

26. The antimicrobial polyester-containing article of claim 14 or 15 further comprising one or more compounds selected from the group consisting of metal salts, carboxyl-containing polymers, and combinations thereof.

27. The polyester-containing article of claim 26 wherein the metal salt is selected from the group consisting of soluble silver salts, soluble copper salts, and soluble zinc salts.

28. The polyester-containing article of claim 14 or 15 wherein the polyester is poly(ethylene terephthalate), poly(trimethylene terephthalate), poly(tetramethylene terephthalate), or a copolymer or blend thereof.

29. The polyester-containing article of claim 16 wherein the article is in the form of a bicomponent fiber consisting essentially of poly(ethylene terephthalate) and poly(trimethylene terephthalate).

30. The polyester-containing article of claim 26 wherein the carboxyl-containing polymer is polyacrylic acid or sodium carboxymethylcellulose.

\* \* \* \* \*

UNITED STATES PATENT AND TRADEMARK OFFICE
CERTIFICATE OF CORRECTION

| | |
|---|---|
| PATENT NO. | : 7,629,000 B2 |
| APPLICATION NO. | : 10/842186 |
| DATED | : December 8, 2009 |
| INVENTOR(S) | : Subramaniam Sabesan |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1340 days.

Signed and Sealed this

Second Day of November, 2010

David J. Kappos
*Director of the United States Patent and Trademark Office*